(12) United States Patent
Morishita et al.

(10) Patent No.: US 8,895,503 B2
(45) Date of Patent: *Nov. 25, 2014

(54) PHARMACEUTICAL COMPOSITION FOR TRANSNASAL ADMINISTRATION OF PEPTIDE HORMONES OR CYTOKINES

(75) Inventors: Mariko Morishita, Tokyo (JP); Kozo Takayama, Tokyo (JP); Reiji Nishio, Kamakura (JP); Nobuo Ida, Kamakura (JP)

(73) Assignee: Toray Industries, Inc., Tokyo (JP)

( * ) Notice: Subject to any disclaimer, the term of this patent is extended or adjusted under 35 U.S.C. 154(b) by 241 days.

This patent is subject to a terminal disclaimer.

(21) Appl. No.: 12/867,701

(22) PCT Filed: Feb. 27, 2009

(86) PCT No.: PCT/JP2009/053648
§ 371 (c)(1),
(2), (4) Date: Oct. 4, 2010

(87) PCT Pub. No.: WO2009/107766
PCT Pub. Date: Sep. 3, 2009

(65) Prior Publication Data
US 2011/0020280 A1    Jan. 27, 2011

(30) Foreign Application Priority Data

Feb. 28, 2008  (JP) .................. 2008-048300

(51) Int. Cl.
| | | |
|---|---|---|
| A61K 38/19 | (2006.01) | |
| A61K 38/28 | (2006.01) | |
| A61K 38/00 | (2006.01) | |
| A61K 38/21 | (2006.01) | |
| C07K 14/435 | (2006.01) | |
| A61K 38/10 | (2006.01) | |
| A61K 9/00 | (2006.01) | |
| A61K 47/42 | (2006.01) | |

(52) U.S. Cl.
CPC ............... *A61K 38/215* (2013.01); *A61K 38/28* (2013.01); *C07K 14/43581* (2013.01); *A61K 38/10* (2013.01); *A61K 9/0043* (2013.01); *A61K 47/42* (2013.01)
USPC .............................. 514/5.9; 514/5.3; 530/300

(58) Field of Classification Search
None
See application file for complete search history.

(56) References Cited

U.S. PATENT DOCUMENTS

| | | | | |
|---|---|---|---|---|
| 4,153,689 | A * | 5/1979 | Hirai et al. ...................... | 514/5.9 |
| 4,789,660 | A * | 12/1988 | Enever et al. ................... | 514/6.5 |
| 6,428,805 | B1 | 8/2002 | Dohi et al. | |
| 6,960,431 | B2 * | 11/2005 | Morham et al. .................. | 435/5 |
| 7,153,931 | B1 * | 12/2006 | Fischer et al. ................. | 530/326 |
| 7,989,419 | B2 * | 8/2011 | Gyurik et al. ................... | 514/5.9 |
| 2004/0147027 | A1 | 7/2004 | Troy et al. | |
| 2005/0042753 | A1 | 2/2005 | Yang et al. | |
| 2006/0003989 | A1 | 1/2006 | Quay et al. | |
| 2007/0105775 | A1 | 5/2007 | Lee et al. | |

FOREIGN PATENT DOCUMENTS

| | | | |
|---|---|---|---|
| JP | 2-42027 A | 2/1990 | |
| JP | 4338313 B2 | 7/2009 | |
| WO | WO-00/01417 A1 | 1/2000 | |
| WO | WO-00/29427 A2 | 5/2000 | |
| WO | WO-2006/044063 A2 | 4/2006 | |
| WO | WO-2006/101283 A1 | 9/2006 | |
| WO | WO-2006/112738 A1 | 10/2006 | |
| WO | WO 2007/014391 A2 | 2/2007 | |
| WO | WO-2008/022046 A2 | 2/2008 | |
| WO | WO2008022046 * | 2/2008 | ............. A61K 47/48 |

OTHER PUBLICATIONS

De Rossi et al. Trojan peptides: the penetratin system for intracellular delivery—Trends in Cell Biol. 8, 84-87, 1998.*
Morishita et al. A novel approach using functional peptides for efficient intestinal absorption of insulin, J. Control. Rel. 118, 177-184, 2007.*
Maitani et al. The inactivation process of fibroblast interferon β in the preparation stage and in rabbit nasal absorption of mixed and freeze-dried powder dosage forms. Int. J. Pharmaceut. 64, 139-146, 1990.*
Decision of Refusal dated May 18, 2010 for Japanese Application No. 2009-510212.
Itoh, "Peptide consisting of 16 amino acids and transcellular drug delivery by Penetratin", Farumashia, 2001, vol. 37, No. 9, pp. 836-837.
Begley D J: "Delivery of therapeutic agents to the central nervous system: the problems and the possibilities", Pharmacology & Therapeutics, Elsevier, GB, vol. 104, 2004, pp. 29-45.
Morishita et al: "Is the oral route possible for peptide and drug delivery?", Drug Discovery Today, Elsevier, US, vol. 11, No. 19-20, Oct. 2006, pp. 905-910.
Kamei et al: "Usefulness of cell-penetrating peptides to improve intestinal insulin absorption", Journal of Controlled Release, Elsevier, NL, vol. 132, 2008, pp. 21-25.
Xin Hua Zhou: "Overcoming enzymatic and absorption barriers to non-parenterally administered protein and peptide drugs", Journal of Controlled Release, Elsevier, NL, vol. 29, 1994, pp. 239-252.
Khafagey et al: "Effect of cell-penetrating peptides on nasal absorption of insulin", Journal of Controlled Release, Elsevier, vol. 133, 2009, pp. 103-108.

* cited by examiner

*Primary Examiner* — Elly-Gerald Stoica
(74) *Attorney, Agent, or Firm* — Birch, Stewart, Kolasch & Birch, LLP (57) ABSTRACT

A method for nasal administration of a pharmaceutical composition comprising a hydrophilic bioactive substance and any one of (a) to (c): (a) a peptide having the amino acid sequence shown in SEQ ID NO:1; (b) a peptide having the same amino acid sequence as shown in SEQ ID NO:1 except that one or several amino acids are deleted, substituted and/or added, the peptide having nasal mucosal permeability; (c) a peptide having an amino acid sequence represented by the reverse sequence of (a) or (b), the peptide having nasal mucosal permeability, with the proviso that a C-terminal amidated peptide is excluded. A hydrophilic bioactive substance having a low transmucosal absorption capability which has conventionally been able to be administered by only injection can be nasally administered. Such a pharmaceutical composition is useful for improvement of the pain and the inconvenience of patients caused by administration by injection.

6 Claims, 8 Drawing Sheets

PHARMACEUTICAL COMPOSITION FOR TRANSNASAL ADMINISTRATION OF PEPTIDE HORMONES OR CYTOKINES

TECHNICAL FIELD

The present invention relates to a pharmaceutical composition to allow migration of a hydrophilic bioactive substance from the nasal cavity into blood while maintaining the activity thereof.

BACKGROUND ART

In addition to low molecular weight hydrophobic drugs which have been mainly employed so far, hydrophilic bioactive substances such as peptides and nucleic acids have recently appeared in clinical sites. They are employed as pharmaceuticals and exhibit remarkable therapeutic effects. However, up to now, in most cases, their administration methods are limited to usage as injection solutions. This is because hydrophilic substances are incapable of passing through the epithelial cell layer of mucosa, unlike known drugs. Since the cells in the epithelial cell layer are closely bound to each other to prevent invasion of foreign substances into the living body, substances having hydrophilicity can hardly pass through the layer, so that oral administration, which is a generally-used administration method of drugs, is incapable of allowing the substances to act inside the body.

Since administration of a drug by injection is a heavy burden on a patient and a physician, particularly in cases where the therapy is frequent and continues for a long time, various methods have been studied to enable administration of such a hydrophilic bioactive substance by a method other than injection.

In oral administration which is widely used as a general method for administration of a drug, there are a number of attempts for technologies to allow absorption of a hydrophilic bioactive substance. In particular, to improve permeability of the intestinal epithelial cell layer which is a major region of absorption when oral administration is carried out, attempts have been made using surfactants, epithelial cell-adhesive substances, cell penetrating peptides and the like.

"Cell penetrating peptide" is a general term for peptides having a property to migrate from outside a cell to inside the cell without destroying the cell membrane. Well-known examples of the peptides include various types of peptides such as oligoarginine having a stretch of arginine; Tat, a peptide of the HIV-1 virus (Patent Literature 1); and penetratin having the same amino acid sequence as shown in SEQ ID NO:1 of the present invention (Patent Literatures 2 and 3). Various peptides are included therein, and examples thereof include those characterized by simple basicity; those having a hydrophobic domain; those characterized by amphiphilicity of the primary structure or secondary structure of the peptides; and those having an uncertain mechanism. Using these peptides, researches on their migration capabilities into the cell, and their uses, as vehicles, for delivery of genes linked to them into the cell have been extensively carried out.

Further, studies aiming to promote penetration through the epithelia cell layer and to promote absorption upon oral administration using such a property have been carried out (Patent Literatures 4 and 5). However, since the absorption promotion effects of the cell penetrating peptides used in these studies are based on evaluation with rinsed intestinal tract and the like, the actual effects upon oral administration are not clear. Further, it is difficult to realize stable absorption because of digestive degradation in stomach and changes in the environment in the gastrointestinal tract by ingestion, so that practical application of oral administration of a hydrophilic bioactive substance has not been achieved.

As a method other than oral administration to realize the absorption, an administration method employing the nasal mucosal layer has been devised. Between nasal mucosa and mucosa of the gastrointestinal tract, there are differences in the types of the cells constituting the mucosal layer and differences in properties of individual cells, and degradative enzymes existing in the lumens show various differences such as differences in their types and amounts, so that technologies other than those for promotion of absorption in the gastrointestinal tract are demanded for promotion of transnasal absorption.

Administration can be easily carried out through nasal mucosa, and nasal mucosa has properties suitable for absorption of drugs because of developed blood vessels and lymph vessels under it. Further, it is considered that, since the drug absorbed from the nasal cavity directly passes into the general circulation after the absorption, the first-pass effect by liver can be avoided, so that the nasal cavity is considered to be effective as an administration site for drugs prone to be metabolized in the gastrointestinal tract and/or liver. However, since, as in the other absorption sites, nasal mucosa has low permeabilities for hydrophilic bioactive substances, and since the area of the absorption site is small, an absorption-promoting technology is required to realize absorption of hydrophilic bioactive substances from the nasal cavity.

There are examples of clinical tests with transnasal formulations using surfactants as absorption-promoting agents by a plurality of drug makers so far, but all of the tests were given up because of strong irritation to nasal mucosa. Further, as a method which does not employ a surfactant, promotion of absorption using a peptide has been attempted at the research phase, and an attempt to promote transnasal absorption by direct linking of a peptide to a drug is disclosed in Patent Literature 6. However, since this technology requires chemical modification of a drug, it necessarily has many problems to be solved such as decrease in the pharmacological activity of the drug, changes in the pharmacokinetics, increase in the production cost and antigenicity of the administered drug.

Possibilities of promotion of transnasal absorption by penetratin or a modified product thereof are mentioned in Patent Literature 2 and 3, but since these require covalent bond between the drug to be allowed to permeate the mucosa and the modified product of penetratin, they are technologies different from the present invention wherein a hydrophilic bioactive substance and penetratin or a modified product thereof are not covalently bonded to each other. It is known that efficient occurrence of desorption from the cell, in addition to migration from outside the cell to inside the cell, is required to realize promotion of nasal absorption using a cell penetrating peptide, and the absorbability upon absorption through nasal mucosa is affected by various factors other than cell permeability such as degradability of the peptide by various degradative enzymes existing in the nasal mucosal tissue. Therefore, necessity for confirmation, by experiments using a model animal or the like, of whether or not the cell penetrating peptide has permeability through nasal mucosa is common general technical knowledge of those skilled in the art. However, since Patent Literatures 2 and 3 do not disclose experimental verification on nasal mucosal permeability of penetratin and the modified product thereof, it is not easy for those skilled in the art to infer from Patent Literature 2 and 3 that penetratin and the modified product thereof have nasal mucosal permeability.

There is also an attempt to administer oligoarginine which is not covalently linked to the drug as a nasal absorption-promoting substance together with the drug (Patent Literature 7), but this requires a high concentration of oligoarginine and its effect has been demonstrated with only a single model drug, fluorescently-labeled dextran, so that permeability of a peptide hydrophilic bioactive substance is unknown.

Thus, a highly-practical technology to enable high efficiency nasal absorption of hydrophilic bioactive substances has not been discovered yet.

[Patent Literature 1] JP 10-33186 A
[Patent Literature 2] Japanese Translated PCT Patent Application Laid-open No. 2002-530059
[Patent Literature 3] Japanese Translated PCT Patent Application Laid-open No. 2002-519392
[Patent Literature 4] JP 2006-257074 A
[Patent Literature 5] JP 2008-7448 A
[Patent Literature 6] WO 2004/037859
[Patent Literature 7] JP 10-95738 A

DISCLOSURE OF THE INVENTION

Problems to be Solved by the Invention

The present invention aims to provide a pharmaceutical composition to allow migration of a nasally administered hydrophilic bioactive substance into blood.

Means for Solving the Problems

To overcome the above-described problems, the present inventors studied a method to improve absorption efficiency of a hydrophilic bioactive substance which has a low migration capability through mucosa into blood under normal conditions, and discovered that a pharmaceutical composition comprising a hydrophilic bioactive substance and: (a) a peptide having the amino acid sequence shown in SEQ ID NO:1, with the proviso that a C-terminal amidated peptide is excluded; (b) a peptide having the same amino acid sequence as shown in SEQ ID NO:1 except that one or several amino acids are deleted, substituted and/or added, the peptide having nasal mucosal permeability, with the proviso that a C-terminal amidated peptide is excluded; or (c) a peptide having an amino acid sequence represented by the reverse sequence of (a) or (b), the peptide having nasal mucosal permeability, with the proviso that a C-terminal amidated peptide is excluded; is effective and can realize highly efficient migration of the hydrophilic bioactive substance into blood upon nasal administration. That is, the present invention has the following constitution.

(1) A pharmaceutical composition for nasal administration comprising a hydrophilic bioactive substance and any one of (a) to (c) below, with the proviso that a C-terminal amidated peptide is excluded:

(a) a peptide having the amino acid sequence shown in SEQ ID NO:1;

(b) a peptide having the same amino acid sequence as shown in SEQ ID NO:1 except that one or several amino acids are deleted, substituted and/or added, the peptide having nasal mucosal permeability; and (c) a peptide having an amino acid sequence represented by the reverse sequence of (a) or (b), the peptide having nasal mucosal permeability.

(2) The pharmaceutical composition for nasal administration according to (1), wherein the peptide in (b) has the same amino acid sequence as shown in SEQ ID NO:1 except that one or several basic amino acids are substituted to another/other basic amino acid(s) or added, the peptide having nasal mucosal permeability.

(3) The pharmaceutical composition for nasal administration according to (1) or (2), wherein the peptide in (b) has the amino acid sequence shown in any one of SEQ ID NOs:3 to 6.

(4) The pharmaceutical composition for nasal administration according to any one of (1) to (3), wherein the peptide in (c) has the amino acid sequence shown in SEQ ID NO:2.

(5) The pharmaceutical composition for nasal administration according to any one of (1) to (4), containing any one of the peptides in (a) to (c) at a concentration of 0.2 to 2.0 mM.

(6) The pharmaceutical composition for nasal administration according to any one of (1) to (5), wherein the hydrophilic bioactive substance is a peptide.

(7) The pharmaceutical composition for nasal administration according to any one of (1) to (6), wherein the hydrophilic bioactive substance is insulin or interferon β.

Effect of the Invention

By the present invention, migration of a nasally-administered hydrophilic bioactive substance into blood is possible, and simpler and more patient-oriented pharmacotherapy is possible compared to the conventional administration method by injection.

BEST MODE FOR CARRYING OUT THE INVENTION

The present invention relates to a pharmaceutical composition for nasal administration to allow migration of a hydrophilic bioactive substance from the nasal cavity into blood, which pharmaceutical composition contains a hydrophilic bioactive substance as a pharmacologically active component and a specific peptide having nasal mucosal permeability that are blended independently and not covalently linked to each other. Here, "hydrophilic bioactive substance" in the present invention means a physiologically active substance which is characteristically hydrophilic. "Hydrophilic" herein means having high solubility into water, and a substance which dissolves into water in an amount of 1 μg or more per 1 ml of water is defined as hydrophilic. "Physiologically active substance" means substances in general which act on a living body and cause changes in the living body, and examples thereof include proteins which bind to receptors on specific cells and enzymes having affinities to substances in the living body. Further, it may be a substance which does not cause a direct reaction with a substance in a living body and includes substances capable of being administered to a living body for medical use, such as dextran which is used as an alternative to blood plasma to increase blood.

"Peptide" in the present invention means a substance having a structure wherein amino acids are linked to each other by peptide bonds. Among peptides, those having a high molecular weight are generally called proteins, but in the present specification, these proteins are also called peptides without being limited by their molecular weights. Further, glycoproteins having a sugar chain linked to a protein, and derivatives having a chemical modification such as polyethylene glycolation (PEGylation) are also included in the peptides in the present invention.

Details of the pharmaceutical composition for nasal administration of the present invention will now be described.

In the present invention, the peptide which is contained together with a hydrophilic bioactive substance and has the amino acid sequence shown in SEQ ID NO:1 is the peptide generally called penetratin. Penetratin is a peptide having cell permeability found at the DNA-binding site of the peptide in *Drosophila* called Antennapedia. The present inventors newly found that nasal administration of penetratin, with the proviso that a C-terminal amidated peptide is excluded, together with a hydrophilic bioactive substance allows migration of the hydrophilic bioactive substance into blood at a high rate in a living body due to the excellent nasal mucosal permeability of penetratin, thereby completing the present invention.

For the peptide having the amino acid sequence of SEQ ID NO:1 used in the present invention, deletion, substitution and/or addition of one or several amino acid(s) is/are acceptable as long as the difference(s) is/are within the range wherein the nasal mucosal permeability required in the present invention is retained as the entire peptide, with the proviso that a C-terminal amidated peptide is excluded. For example, cases where a basic amino acid(s) in the peptide is/are substituted with another or other several basic amino acid(s), cases where a hydrophilic amino acid(s) is/are substituted with another or other plurality of hydrophilic amino acid(s), and cases where a hydrophobic amino acid(s) is/are substituted with another or other plurality of hydrophobic amino acid(s) in the peptide do not change the properties of the entire peptide, and therefore these are accepted without problems. In particular, cases where one or several basic amino acid(s) is/are substituted in or added to the amino acid sequence shown in SEQ ID NO:1 are preferably accepted. The number of the deletion(s), substitution(s) and/or addition(s) of the above-described amino acids is preferably small, and preferably 1 to 5 amino acid(s), more preferably 1 to 3 amino acid(s), still more preferably 1 amino acid is/are involved therein. Here, in the present invention, "hydrophobic amino acid" means an amino acid selected from the group consisting of leucine, isoleucine, tryptophan, phenylalanine, valine and alanine, and "hydrophilic amino acid" means an amino acid selected from the group consisting of serine, threonine, aspartic acid, glutamic acid, lysine, arginine and histidine. "Basic amino acid" means an amino acid selected from the group consisting of lysine, arginine and histidine.

Preferred examples of the peptide having the same amino acid sequence as shown in SEQ ID NO:1 except that one or several amino acids are deleted, substituted and/or added, which peptide has nasal mucosal permeability include the peptide having the amino acid sequences shown in any one of SEQ ID NOs:3 to 6.

In the present invention, even if the peptide contained together with a hydrophilic bioactive substance is a peptide represented by the reverse sequence of either a peptide having the amino acid sequence shown in SEQ ID NO:1 which exhibits an effective transnasal mucosal permeability or a peptide having the same amino acid sequence as shown in SEQ ID NO:1 except that a part of amino acids are deleted, substituted and/or added, it is acceptable as long as the difference is within the range wherein the nasal mucosal permeability required in the present invention is retained as the entire peptide. Here, the peptide represented by the reverse sequence means that the sequence of the amino acids constituting the peptide is reversed. For example, when the sequence of the amino acids in a peptide from the N terminus to the C terminus is arginine, glutamine, isoleucine and lysine, the reversed peptide thereof has the amino acid sequence of, from the N terminus to the C terminus, lysine, isoleucine, glutamine and arginine. Preferred examples thereof include the peptide represented by the reverse sequence of a peptide having the amino acid sequence shown in SEQ ID NO:1 (SEQ ID NO:2).

In the present invention, as the amino acids constituting the peptide contained together with a hydrophilic bioactive substance, naturally occurring L-amino acids as well as non-naturally occurring amino acids such as a derivative produced by modification of a part of a naturally occurring amino may be used. For example, since D-amino acids are hardly degraded by proteases, they may be effectively used, and therefore the amino acid sequence of the peptide may be either partially or entirely constituted by D-amino acids, and appropriately selected depending on the hydrophilic bioactive substance administered together with the peptide. In cases where the hydrophilic bioactive substance has negative charges as the whole, the total amino acid sequence is preferably constituted by L-amino acids. For example, when the hydrophilic bioactive substance is insulin, the total amino acid sequence is preferably constituted by L-amino acids. In cases where the hydrophilic bioactive substance does not have charges, or in cases where it has positive charges, the total amino acid sequence is preferably constituted by D-amino acids. For example, in the case of interferon β having positive charges, the total amino acid sequence is preferably constituted by D-amino acids.

In the present invention, the peptide contained together with a hydrophilic bioactive substance may be prepared by a conventional method for synthesizing a peptide, and may also be prepared, for example, by introduction of a gene encoding the amino acid sequence of the peptide into a microorganism such as *E. coli*, animal cells, insect cells or the like and allowing expression of the gene. Further, the peptide may also be obtained by degradation of a protein having the amino acid sequence of the peptide occurring naturally. For example, the peptide having the amino acid sequence shown in SEQ ID NO:1 has partially the same sequence as the Antennapedia protein in *Drosophila*, and it may also be prepared by protease treatment of the protein occurring naturally.

In the present invention, either a single type or a plurality of types of the peptide(s) may be contained together with a hydrophilic bioactive substance, and a single type of the peptide is preferred. The concentration thereof is not limited, and as shown in Examples, it is preferably 0.2 to 2 mM. A concentration of 0.5 to 2 mM is more preferred since remarkable nasal permeation of a hydrophilic bioactive substance is observed therewith. The concentration of a peptide in the present invention means the concentration of the peptide upon its administration to the nasal cavity, and in cases where the pharmaceutical composition of the present invention is a solution, it means the concentration in the solution, and in the case of a solid, it means the concentration obtained when the dose of the composition per administration is restored to 40 µl of a solution which is a standard volume for a single nasal administration.

Specific examples of the hydrophilic bioactive substance used in the present invention include peptides, sugar chains and nucleic acids, and it is preferably a peptide. Specific examples of the peptide include antibodies, peptide hormones and cytokines, and it is preferably a peptide hormone or a cytokine. Examples of the peptide hormone include insulin, calcitonin, parathyroid hormone, growth hormone, GLP-1 and Exendin-4; and examples of the cytokine include interferons, interleukins and G-CSF; and it is preferably insulin or interferon β. Each of these hydrophilic bioactive substances may be either a naturally-occurring substance or a derivative produced by modification of a part of the structure of the sequence thereof. Further, it may be a derivative produced by a chemical modification such as polyethylene glycolation (PEGylation).

The nasal absorption of a hydrophilic bioactive substance in the present invention means migration of the hydrophilic bioactive substance administered to the nasal cavity, from the nasal cavity into blood. Its result can be confirmed by observation of increase in the blood level of the hydrophilic bioactive substance or expression of pharmacological activity thereof. The blood level of the hydrophilic bioactive substance can be measured by a method conventionally used by those skilled in the art, such as an immunoassay. The pharmacological activity can be measured by using as an index, in the case of an enzyme, its enzyme activity; and in the case of a substance which acts on a receptor on the cell, its ability to change a function of the target cell or the amount of production of a marker substance. For example, the pharmacological activity of insulin can be measured by using as an index the blood glucose level of the animal to which insulin was administered.

Whether or not the absorption is promoted can be confirmed by comparison between: the ratio of the amount of migration of the drug into blood with respect to the amount of the drug administered observed when the hydrophilic bioactive substance, which is a pharmacologically active component, was solely administered to the nasal cavity; and the ratio of the amount of migration of the drug into blood with respect to the amount of the drug administered observed when the pharmaceutical composition of the present invention was also administered. If the latter rate is higher, the absorption can be confirmed to have been promoted. To allow exertion of a sufficient function as an actual pharmaceutical agent, the bioavailability value, which indicates the percentage of the AUC (area under the blood concentration versus time curve) value with respect to the AUC upon administration of the same amount of the hydrophilic bioactive substance by injection, of the pharmaceutical composition is preferably not less than 10%, more preferably not less than 20%.

The pharmaceutical composition for nasal administration of the present invention may also contain a pharmaceutically acceptable carrier and/or additive. Examples of such a carrier and additive include water, pharmaceutically acceptable organic solvents, collagen, polyvinyl alcohol, polyvinyl pyrrolidone, carboxyvinyl polymers, sodium carboxymethylcellulose, sodium polyacrylate, sodium alginate, water-soluble dextran, sodium carboxymethyl starch, pectin, methyl cellulose, ethyl cellulose, xanthan gum, gum arabic, casein, gelatin, agar, diglycerol, propylene glycol, polyethylene glycol, vaseline, paraffin, stearyl alcohol, stearic acid, human serum albumin (HSA), mannitol, sorbitol, lactose and surfactants acceptable as pharmaceutical additives.

The pharmaceutical composition for nasal administration of the present invention may be used in various forms such as a solution, solid or powder, but in view of stability and ease of handling, a form of solid or powder produced by a method such as freeze-drying is preferred.

The method for administering the pharmaceutical composition for nasal administration of the present invention to animals (including human) is not restricted in terms of its specific form. For example, the composition in a dry state or in the form of a solution may be administered as it is; the composition may be filled in a capsule together with a vehicle and then administered; or the composition in a dry state may be once dissolved or dispersed in water and then administered.

The dose and the number of doses upon administration of the pharmaceutical composition for nasal administration of the present invention to a living body are appropriately selected depending on the dosage form, age and body weight of the patient, and severity of the symptoms, and the composition may be normally administered at a dose within the range of 0.0001 to 50 mg, preferably within the range of 0.001 to 20 mg per adult per day based on the weight of the hydrophilic bioactive substance contained.

EXAMPLES

Example 1

Nasal Administration of Insulin

<Method>

A prescribed amount of insulin (Wako Pure Chemicals) powder was scaled and placed into a 1.5 ml tube (Eppendorf), followed by dissolving it in 0.1 N HCl and then addition of the same amount of 0.1 N NaOH to prepare an insulin solution.

Penetratin (SEQ ID NO:1; synthesis thereof was entrusted to Sigma Genosys) or oligoarginine (SEQ ID NO:7; synthesis thereof was entrusted to Sigma Genosys) having an amino acid sequence constituted entirely by L-amino acids or by D-amino acids was dissolved in PBS and combined with the above-mentioned insulin solution to prepare, for each administration experiment, 40 µl of a mixed solution containing insulin (10 IU/kg) and 0.5 mM of each peptide.

Male SD rats having a body weight of about 200 g were fasted for 24 hours and anesthetized by intraperitoneal injection of 50 mg/kg of pentobarbital, followed by incision of the cervical part to expose trachea. A polyethylene tube (INTRAMEDIC PE205, Clay Adams) was inserted into trachea, and esophagus was partially incised and a tube having the same diameter was carefully inserted from the incised part of the esophagus to choanae without damaging tissues. The tip of the tube to be inserted into the choanae was preliminarily tightly sealed with absorbent cotton and an adhesive. To prevent leakage of the drug solution, the nasopalatine duct in maxilla opening into the oral cavity was closed with a synthetic adhesive (Aron Alpha A; manufactured by Daiichi Sankyo Company, Limited). From the jugular vein, 0.25 ml of blood was collected before and 5, 10, 15, 30, 60, 120, 180 and 240 minutes after administration of the prepared mixed solution of insulin and the peptide, or only insulin, followed by centrifugation to separate blood plasma and measuring the plasma insulin concentration by EIA kit (Levis). The bioavailability was calculated by comparison with data obtained by subcutaneous administration of insulin.

<Results>

Figure 1:
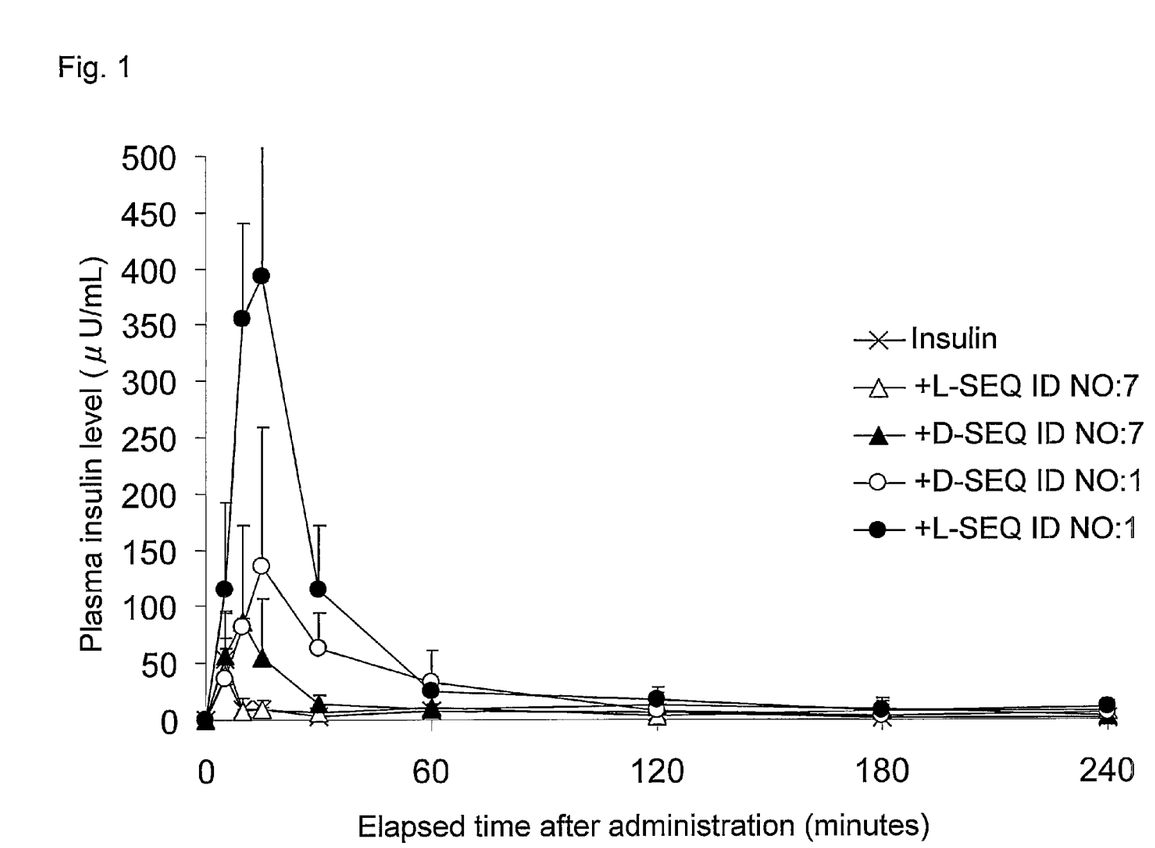
FIG. 1 shows the absorption promotion effect on nasally administered insulin, obtained by using the peptide of SEQ ID NO:1 or SEQ ID NO:7: blood level.
Figure 2:
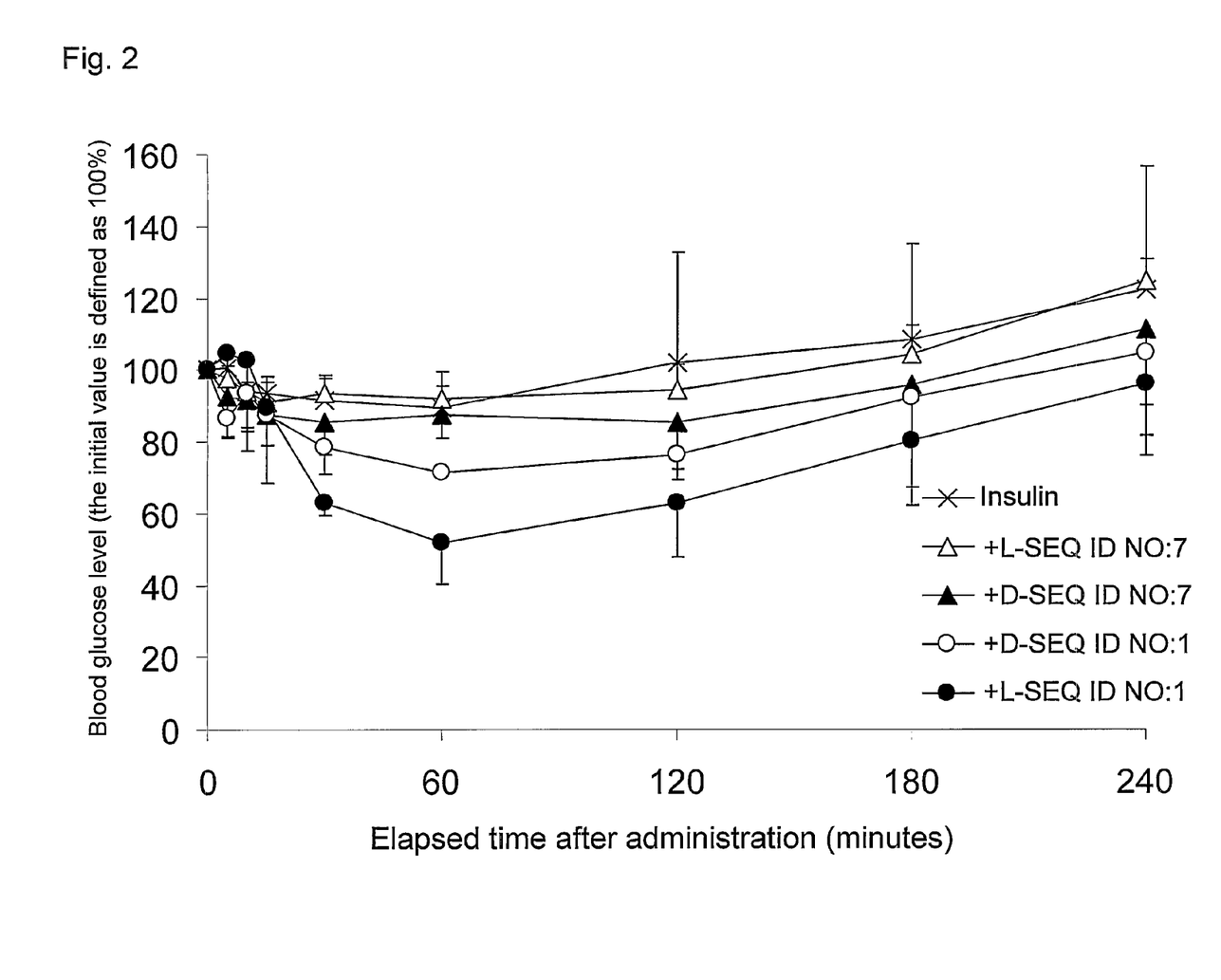
FIG. 2 shows the absorption promotion effect on nasally administered insulin, obtained by using the peptide of SEQ ID NO:1 or SEQ ID NO:7: blood glucose level.

Changes in the blood insulin level with time are shown in FIG. 1, and changes in the blood glucose level are shown in FIG. 2. Rats to which only insulin was nasally administered hardly exhibited increase in the blood insulin level, while in rats to which penetratin or oligoarginine was administered together with insulin, migration of insulin into blood was observed from immediately after the administration. The highest maximum blood level was achieved with L-penetratin, and this was followed in order by D-penetratin, D-oligoarginine and L-oligoarginine (FIG. 1). Decrease in the blood glucose level, which is a pharmacological activity caused by migration of insulin into blood, was observed, and decrease in the blood glucose level reflecting the blood insulin level was confirmed (FIG. 2).

Figure 3:
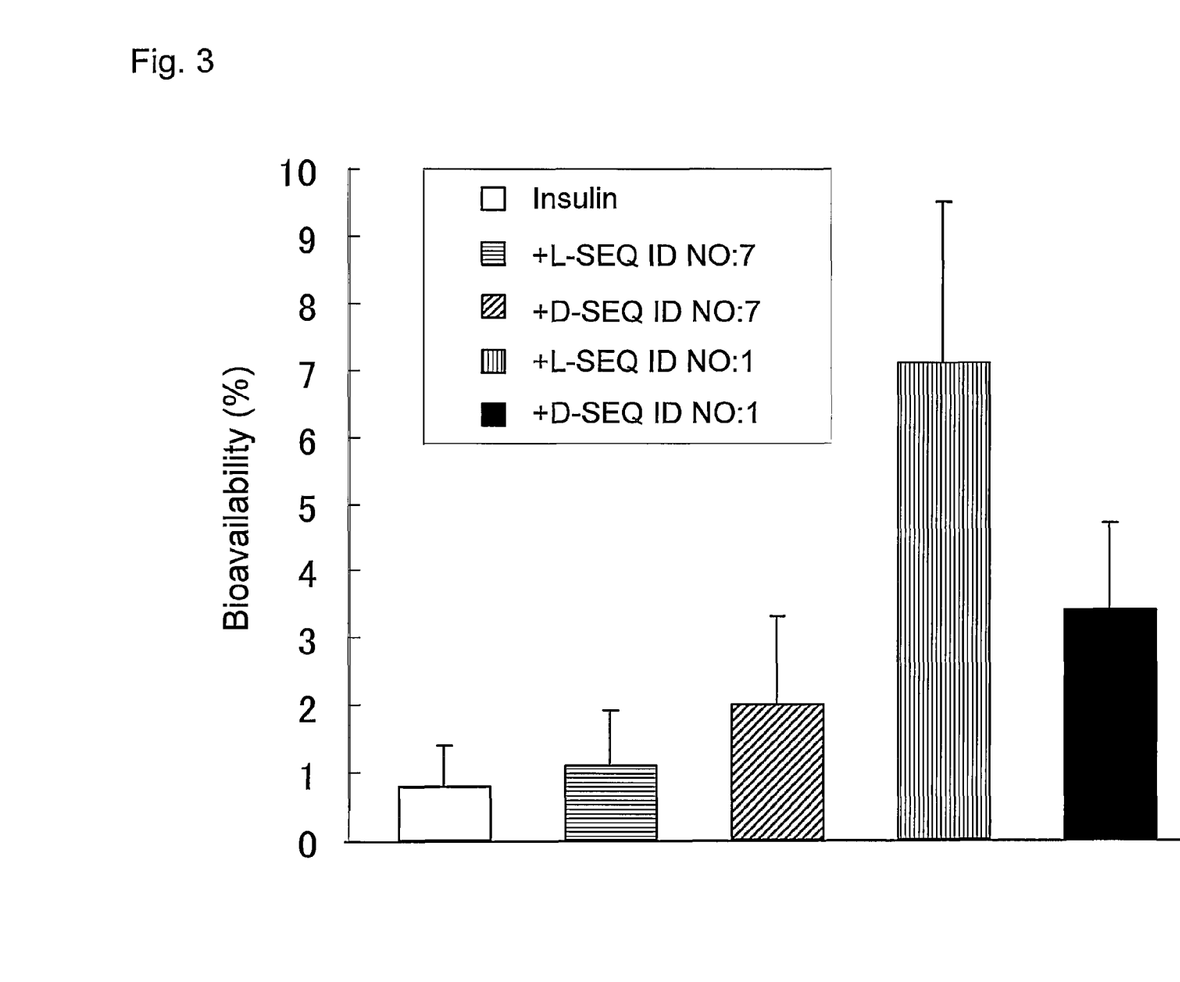
FIG. 3 shows the absorption promotion effect on nasally administered insulin, obtained by using the peptide of SEQ ID NO:1 or SEQ ID NO:7: bioavailability.

The bioavailability was 0.8% in rats to which only insulin was administered, while in the cases of simultaneous administration of insulin and L- or D-oligoarginine, the bioavailability (BA) was 1.1% for L-oligoarginine and 2.0% for D-oligoarginine, and in the cases of simultaneous administration of insulin and penetratin, the BA was 3.4% for D-penetratin and 7.1% for L-penetratin (FIG. 3), showing that penetratin has a higher insulin absorption promotion effect compared to oligoarginine.

Example 2

Nasal Administration of Insulin and its Dependency on Peptide Concentration

<Method>

L-penetratin (SEQ ID NO:1), which showed the highest efficiency of the absorption promotion effect in Example 1, was similarly evaluated in the same manner as in Example 1 except that its concentration in the solution to be administered was changed to 0.2 mM, 0.5 mM, 1 mM or 2 mM.

<Results>

Figure 4:
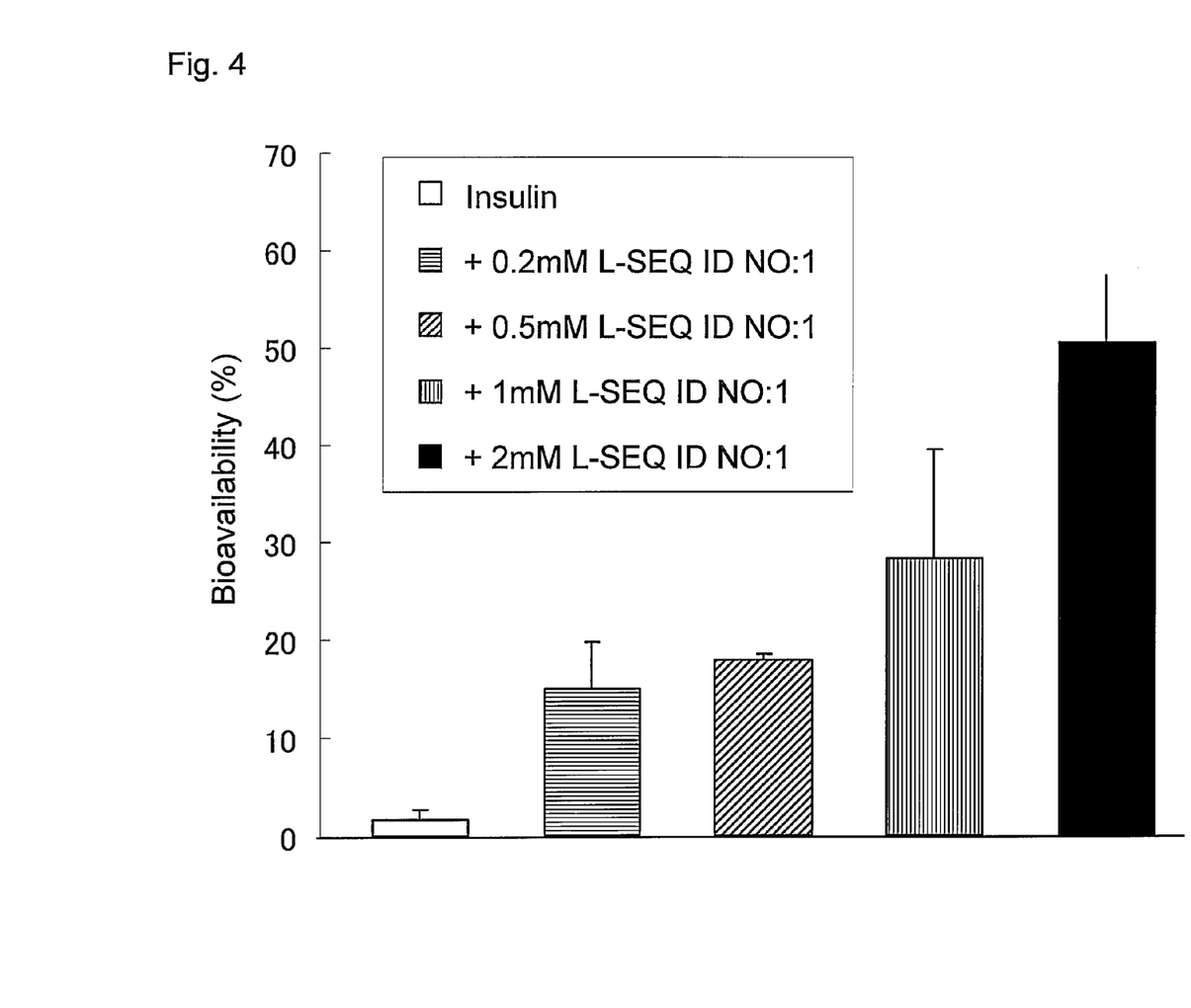
FIG. 4 shows the absorption promotion effect on nasally administered insulin, obtained by using the peptide of SEQ ID NO:1: concentration dependency.

While the bioavailability in the case of administration of only insulin was 1.7%, the bioavailabilities in the cases of administration of 0.2 mM, 0.5 mM, 1 mM and 2 mM L-penetratin were 15.1%, 17.9%, 28.4% and 50.7%, respectively. Thus, the absorption efficiency of insulin was improved dependently on the concentration of penetratin (FIG. 4).

Example 3

Nasal Administration of Fluorescently-Labeled Dextran

<Method>

A fluorescently-labeled dextran FD-4 (Molecular probes, Inc.) was diluted with PBS to provide a 4 mg/ml solution. Using 40 μl of this solution, the evaluation was carried out in the same manner as in Example 1. The FD concentration in blood was quantified by fluorometry. The bioavailability was calculated by comparison with the case where the same amount of FD-4 was intravenously administered.

<Results>

The bioavailability was 4.9% in the rats to which only FD-4 was administered, 17% in the case of usage of L-penetratin, and 36% in the case of usage of D-penetratin. The bioavailabilities in the rats to which L-oligoarginine and D-oligoarginine were administered were 12.4% and 12.4%, respectively.

Figure 5:
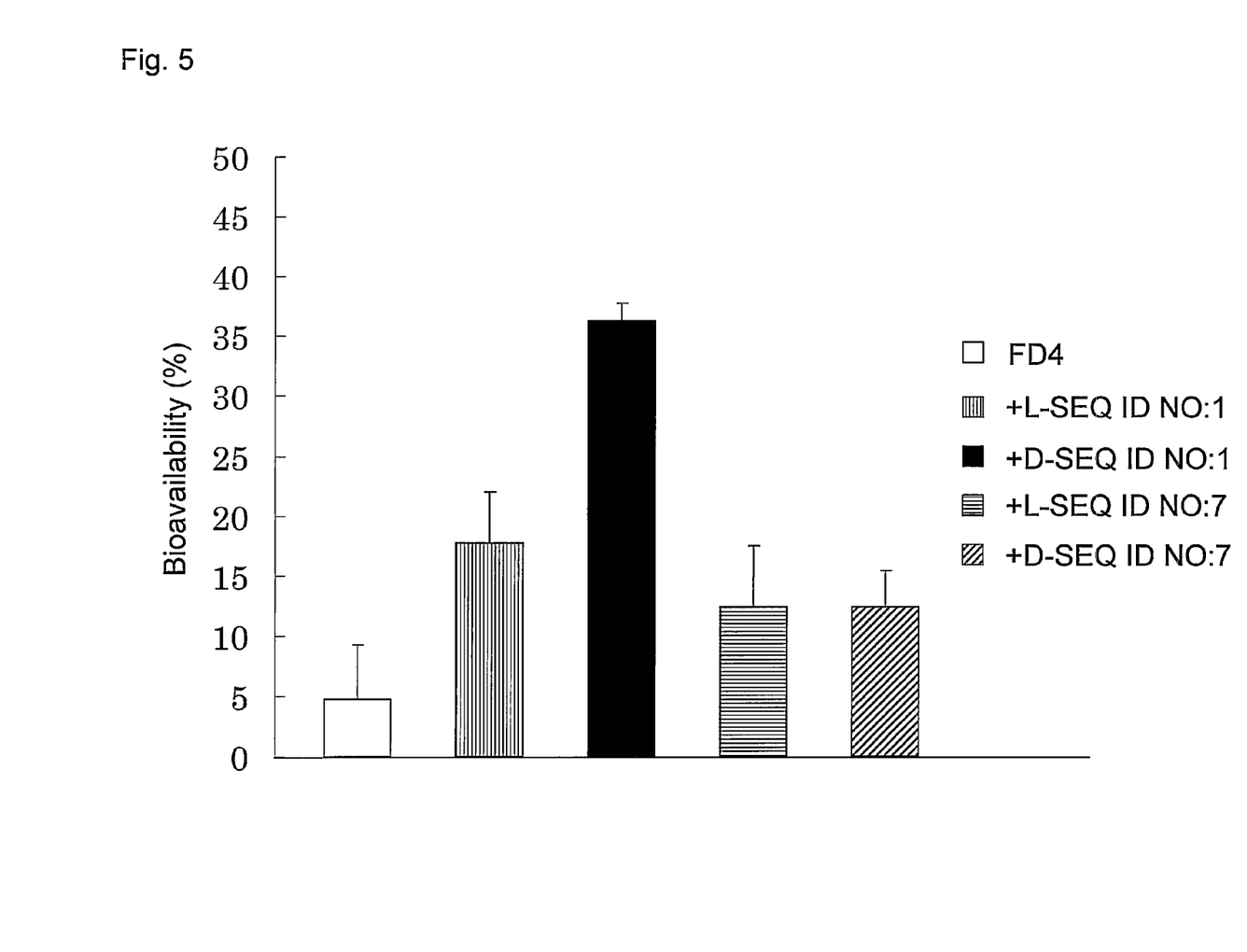
FIG. 5 shows the absorption promotion effect on nasally administered fluorescently labeled dextran, obtained by using the peptide of SEQ ID NO:1.

Thus, penetratin exhibited a higher absorption promotion effect compared to oligoarginine (FIG. 5).

Example 4

Nasal Administration of Interferon β

<Method>

With ice cooling, 1 ml of PBS supplemented with Tween 20 was added to human wild-type interferon β ("Feron" manufactured by Toray Industries, Inc.) to obtain a 6,000,000 IU/ml solution, and a 100 μl aliquot of the resulting solution was taken. To this aliquot, 566 μl of PBS supplemented with Tween 20 was added to obtain a 900,000 IU/ml solution. Each of D-penetratin and L-penetratin (SEQ ID NO:1) was scaled, and 40 μl of the interferon β solution was added thereto such that the final concentration of 0.5 mM or 2 mM was attained, to obtain a mixed solution of interferon β and penetratin, which was then evaluated in the same manner as in Example 1. The concentration of interferon β was measured by "Human Interferon β ELISA Kit" manufactured by Kamakura Techno-Science Inc., and the bioavailability was calculated by comparison of its plasma concentration with that of the case where the same amount of interferon β was intravenously administered.

<Results>

Figure 6:
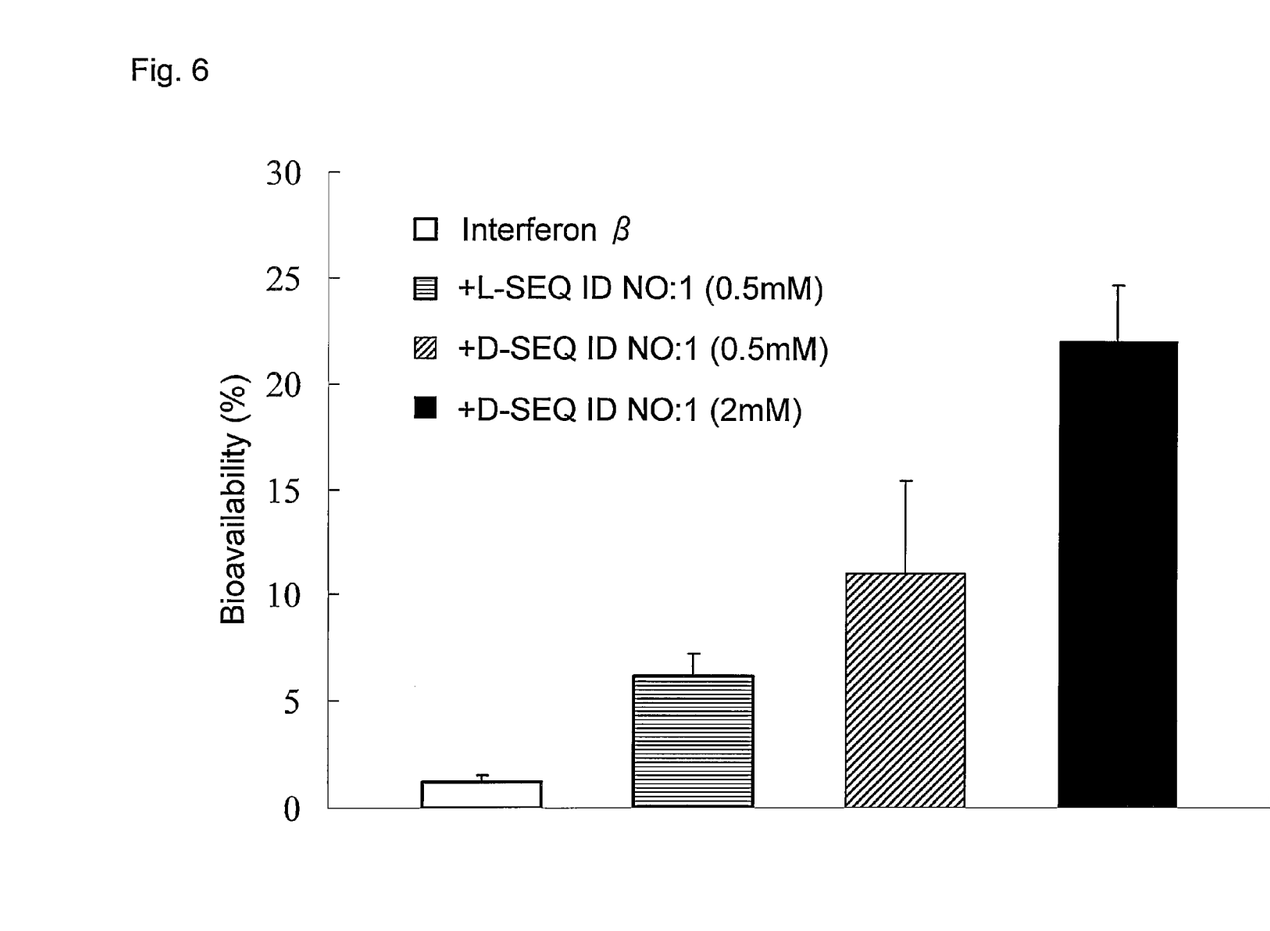
FIG. 6 shows the absorption promotion effect on nasally administered interferon β, obtained by using the peptide of SEQ ID NO:1.

By addition of penetratin together with interferon β, migration of interferon β into blood was observed. The bioavailability was 6.1% for 0.5 mM L-penetratin, 11.0% for 0.5 mM D-penetratin, and 22.0% for 2 mM D-penetratin (FIG. 6).

Example 5

Nasal Administration of Insulin

<Method>

A prescribed amount of insulin (Wako Pure Chemicals) powder was scaled and placed into a 1.5 ml tube (Eppendorf), followed by dissolving it in 0.1 N HCl and then addition of the same amount of 0.1 N NaOH to prepare an insulin solution.

Each of the peptides having an amino acid sequence constituted entirely by L-amino acids (SEQ ID NOs:1 to 6; synthesis thereof was entrusted to Sigma Genosys) was dissolved in PBS and combined with the above-mentioned insulin solution to prepare, for each administration experiment, 40 μl of a mixed solution containing insulin (1 IU/kg) and 0.5 mM of each peptide. The prepared solutions were subjected to the evaluation in the same manner as in Example 1.

<Results>

Figure 7:
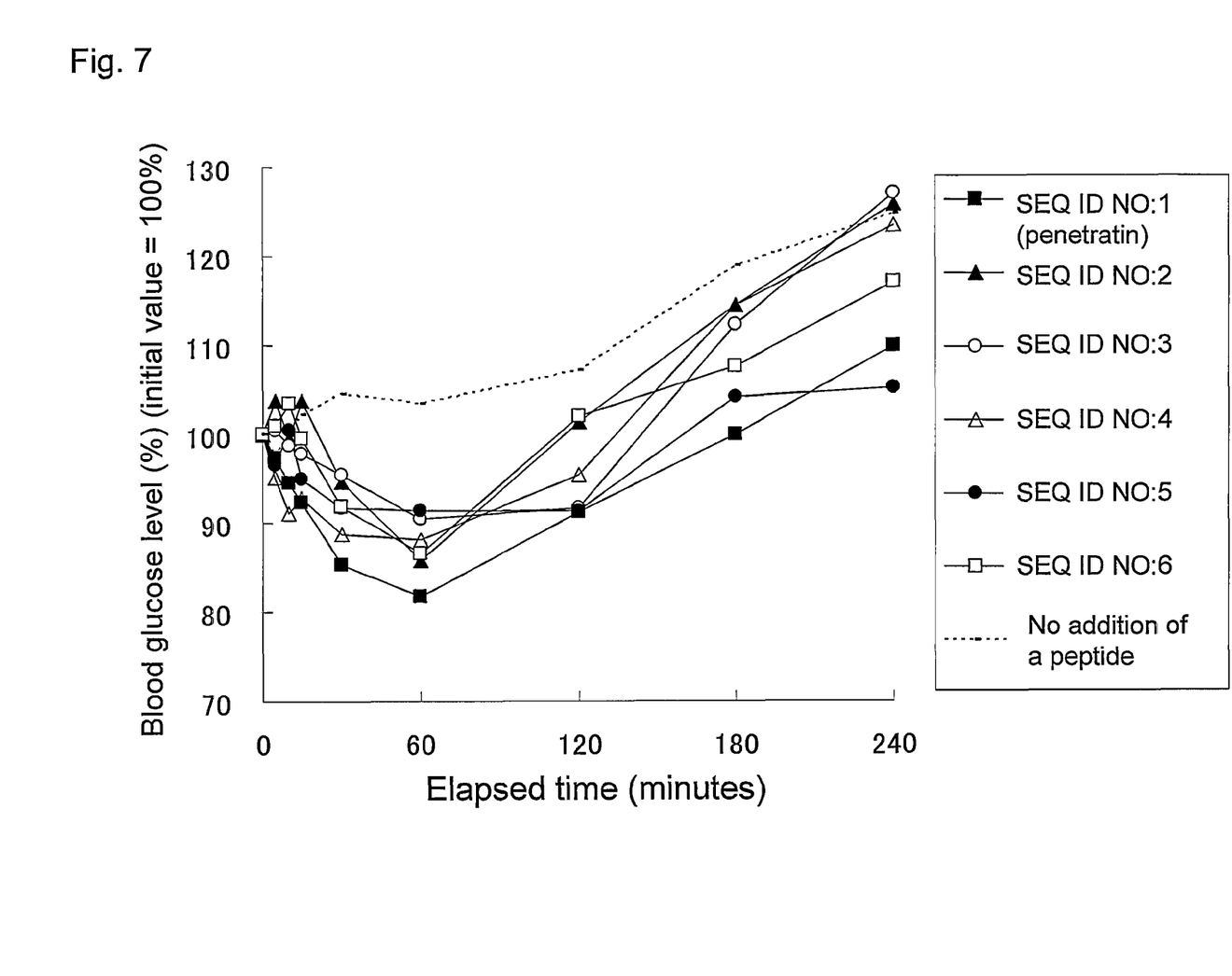
FIG. 7 shows the absorption promotion effect on nasally administered insulin, obtained by using the peptides of SEQ ID NOs:1 to 6: blood glucose level.
Figure 8:
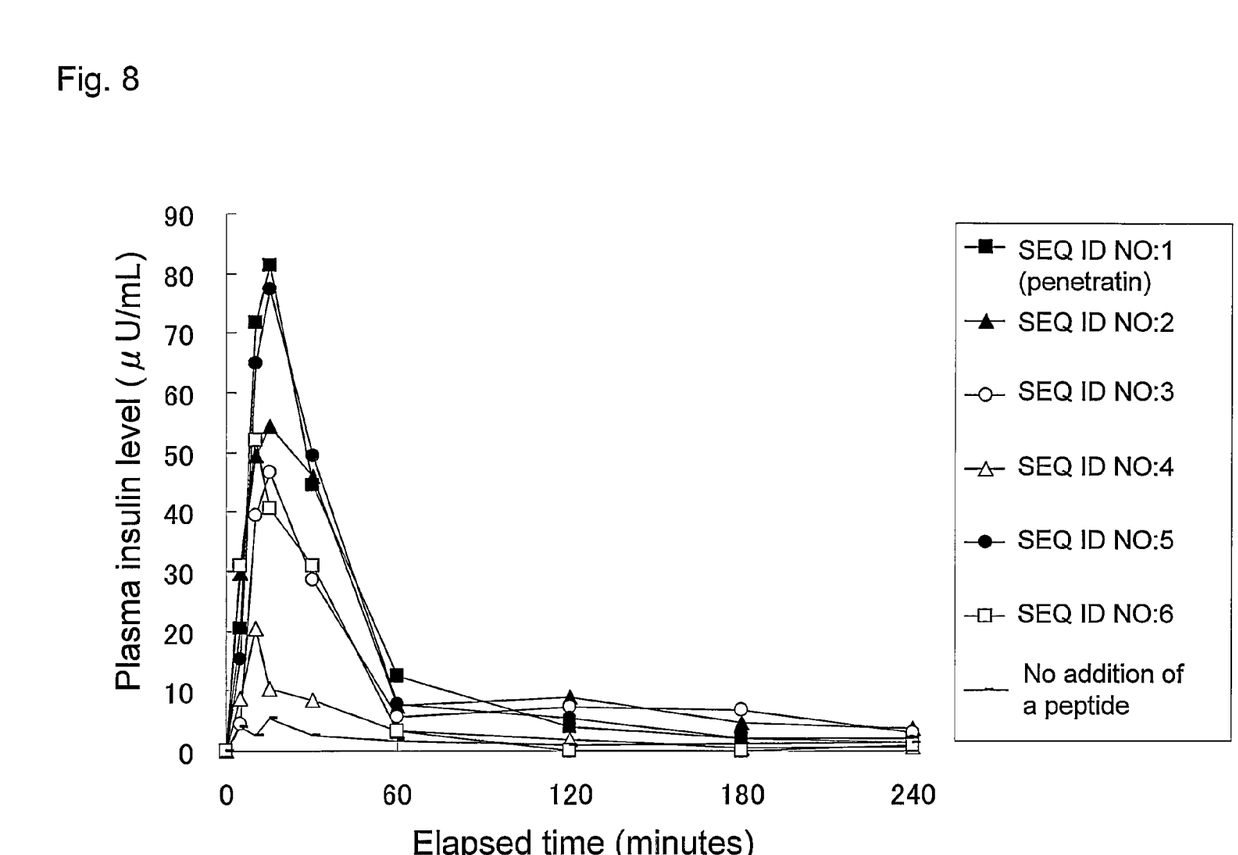
FIG. 8 shows the absorption promotion effect on nasally administered insulin, obtained by using the peptides of SEQ ID NOs:1 to 6: blood level.

Changes in the blood glucose level with time are shown in FIG. 7; changes in the blood insulin level with time are shown in FIG. 8; and various parameters obtained by the evaluation results are shown in Table 1. The increase in the blood insulin level could be hardly observed in rats to which only insulin was nasally administered, while simultaneous administration of each of the peptides of SEQ ID NO:1 to 6 with insulin caused migration of insulin into blood from immediately after the administration, leading to the decrease in the blood glucose level. The bioavailability (BA) calculated based on the changes in the blood insulin level was 2.3% in rats to which only insulin was administered, while it was 4.4 to 20.1% in the cases with the peptides of SEQ ID NOs:1 to 6. The pharmaceutical availability (PA) calculated based on the changes in the blood glucose level was 4.7% in the case of administration of only insulin, but 15.7% to 37.5% in the cases with the peptides of SEQ ID NOs:1 to 6.

TABLE 1

| | Cmax (μU/mL) | Tmax (min) | AAC (% glu. reduc. h) | AUC (μU·h./mL) | PA (%) | BA (%) |
|---|---|---|---|---|---|---|
| SEQ ID NO: 1 (penetratin) | 92.9 | 13.3 | 34.5 | 54.5 | 37.5 | 19.8 |
| SEQ ID NO: 2 | 58.3 | 11.7 | 13.5 | 52.8 | 14.7 | 19.2 |
| SEQ ID NO: 3 | 49.3 | 18.3 | 17.1 | 43.6 | 18.6 | 15.9 |
| SEQ ID NO: 4 | 21.2 | 11.3 | 10.3 | 12.2 | 11.2 | 4.4 |
| SEQ ID NO: 5 | 100.8 | 16.0 | 21.5 | 52.3 | 23.4 | 19.0 |
| SEQ ID NO: 6 | 187.3 | 10.0 | 14.4 | 55.2 | 15.7 | 20.1 |
| No addition of penetratin | 6.5 | 10.8 | 4.3 | 6.4 | 4.7 | 2.3 |

INDUSTRIAL APPLICABILITY

By the present invention, hydrophilic bioactive substances which have been administered so far as injection solutions can be nasally administered, and therefore drugs which largely improve the pain and the inconvenience of patients can be provided. Improvement of the pain and the inconvenience of hospital visits of patients caused by these injection solutions may not only realize patient-oriented health care in clinical sites but also drastically change the conventional concept of formulation, leading to creation of epoch-making formulations.

The invention claimed is:

1. A method for nasal administration of a drug comprising administering to the nasal mucosa of a patient in need thereof an effective amount of the pharmaceutical composition comprising a mixture of a peptide hormone or cytokine and any one of (a) to (c) below, with the proviso that a C-terminal amidated peptide is excluded:
   (a) a peptide having the amino acid sequence shown in SEQ ID NO:1;
   (b) a peptide having the same amino acid sequence as shown in SEQ ID NO:1, except that one or several amino acids are deleted, substituted and/or added, said peptide having nasal mucosal permeability; and
   (c) a peptide having an amino acid sequence represented by the reverse sequence of (a) or (b), said peptide having nasal mucosal permeability
   wherein the peptide hormone or cytokine is not covalently bonded to any of (a) to (c).

2. The method according to claim 1, wherein said peptide in (b) has the amino acid sequence shown in any one of SEQ ID NOs:3 to 6.

3. The method according to claim 1, wherein any one of said peptides in (a) to (c) are present at a concentration of 0.2 to 2.0 mM.

4. The method according to claim 1, wherein said peptide hormone or cytokine is insulin or interferon β.

5. The method according to claim 1, wherein said peptide in (c) has the amino acid sequence shown in SEQ ID NO:2.

6. The method according to claim 1, wherein said peptide in (b) has the same amino acid sequence as shown in SEQ ID NO:1 except that one or several basic amino acids are substituted by another/other basic amino acid(s) or added, said peptide having nasal mucosal permeability.

* * * * *

SEQUENCE LISTING

<160> NUMBER OF SEQ ID NOS: 7

<210> SEQ ID NO 1
<211> LENGTH: 16
<212> TYPE: PRT
<213> ORGANISM: Drosophila

<400> SEQUENCE: 1

Arg Gln Ile Lys Ile Trp Phe Gln Asn Arg Arg Met Lys Trp Lys Lys
1               5                   10                  15

<210> SEQ ID NO 2
<211> LENGTH: 16
<212> TYPE: PRT
<213> ORGANISM: Artificial Sequence
<220> FEATURE:
<223> OTHER INFORMATION: Synthetic peptide: penetratin reverse

<400> SEQUENCE: 2

Lys Lys Trp Lys Met Arg Arg Asn Gln Phe Trp Ile Lys Ile Gln Arg
1               5                   10                  15

<210> SEQ ID NO 3
<211> LENGTH: 16
<212> TYPE: PRT
<213> ORGANISM: Artificial Sequence
<220> FEATURE:
<223> OTHER INFORMATION: Synthetic peptide: K to R

<400> SEQUENCE: 3

Arg Gln Ile Arg Ile Trp Phe Gln Asn Arg Arg Met Arg Trp Arg Arg
1               5                   10                  15

<210> SEQ ID NO 4
<211> LENGTH: 16
<212> TYPE: PRT
<213> ORGANISM: Artificial Sequence
<220> FEATURE:
<223> OTHER INFORMATION: Synthetic peptide: R to K

<400> SEQUENCE: 4

Lys Gln Ile Lys Ile Trp Phe Gln Asn Lys Lys Met Lys Trp Lys Lys
1               5                   10                  15

<210> SEQ ID NO 5
<211> LENGTH: 16
<212> TYPE: PRT
<213> ORGANISM: Artificial Sequence
<220> FEATURE:
<223> OTHER INFORMATION: Synthetic peptide: K to R, R to K

```
<400> SEQUENCE: 5

Lys Gln Ile Arg Ile Trp Phe Gln Asn Lys Lys Met Arg Trp Arg Arg
1               5                   10                  15

<210> SEQ ID NO 6
<211> LENGTH: 20
<212> TYPE: PRT
<213> ORGANISM: Artificial Sequence
<220> FEATURE:
<223> OTHER INFORMATION: Synthetic peptide: C-R4

<400> SEQUENCE: 6

Arg Gln Ile Lys Ile Trp Phe Gln Asn Arg Arg Met Lys Trp Lys Lys
1               5                   10                  15

Arg Arg Arg Arg
            20

<210> SEQ ID NO 7
<211> LENGTH: 8
<212> TYPE: PRT
<213> ORGANISM: Artificial Sequence
<220> FEATURE:
<223> OTHER INFORMATION: Synthetic peptide: oligo-arginine

<400> SEQUENCE: 7

Arg Arg Arg Arg Arg Arg Arg Arg
1               5
```